United States Patent [19]
McLeod et al.

[11] Patent Number: 6,022,349
[45] Date of Patent: Feb. 8, 2000

[54] METHOD AND SYSTEM FOR THERAPEUTICALLY TREATING BONE FRACTURES AND OSTEOPOROSIS

[75] Inventors: Kenneth J. McLeod, Stony Brook; Clinton T. Rubin, Port Jefferson, both of N.Y.

[73] Assignee: Exogen, Inc., Piscataway, N.J.

[21] Appl. No.: 09/323,976

[22] Filed: Jun. 2, 1999

Related U.S. Application Data

[62] Division of application No. 09/022,454, Feb. 12, 1998
[60] Provisional application No. 60/037,682, Feb. 12, 1997.

[51] Int. Cl.[7] .................................................. A61B 17/56
[52] U.S. Cl. .............................................. 606/58; 606/60
[58] Field of Search .................... 607/51, 52; 606/58, 606/53, 54, 60

[56] References Cited

U.S. PATENT DOCUMENTS

| | | | |
|---|---|---|---|
| Re. 35,129 | 12/1995 | Pethica et al. | 607/52 |
| 4,432,361 | 2/1984 | Christensen et al. | 607/52 |
| 4,889,111 | 12/1989 | Ben-Dov | 607/51 |
| 5,191,880 | 3/1993 | McLeod et al. | 607/51 |

*Primary Examiner*—William E. Kamm
*Attorney, Agent, or Firm*—Dilworth & Barrese

[57] ABSTRACT

A system for therapeutic treatment of bone includes a source of energy for stimulating a bone, a feedback loop for receiving response information from the bone generated by the stimulation and an adjustment device for adjusting the energy source according to predetermined criteria. A method of therapeutically treating bone includes the steps of providing a source of energy for stimulating a bone, feedback means for receiving response information from the bone generated by the stimulation and adjustment means for adjusting the energy source according to predetermined criteria, applying energy to cyclically stimulate the bone, collecting response information from the bone due to the stimulation, comparing the response information to the predetermined criteria and adjusting the energy source to obtain a response in accordance with the predetermined criteria. The system and method ensure, augment and accelerate the bone healing process.

12 Claims, 5 Drawing Sheets

METHOD AND SYSTEM FOR THERAPEUTICALLY TREATING BONE FRACTURES AND OSTEOPOROSIS

CROSS REFERENCE TO RELATED APPLICATION

This application claims priority to Provisional Application Ser. No. 60/037,682 filed Feb. 12, 1997, which is incorporated herein by reference and a division of Ser. No. 09/022,454 Feb. 12, 1998.

BACKGROUND OF THE INVENTION

1. Field of the Invention

This disclosure relates to a system and method for treating bone fractures, bony ingrowth and osteoporosis, and in particular, to a dynamic system and method for applying high frequency, low stress stimulation to a fracture site for accelerating the healing process and improving bone strength.

2. Description of Related Art

Weakened bone structure and improperly healed or slowly healing bone fractures may result in reduced quality of life. Quality of life may be improved for patients with bone fractures by ensuring rapid healing and by inhibiting the loss of bone mineral content (bone mass), and therefore bone strength, associated with fractures. Metabolic bone diseases, such as osteoporosis, also reduce the quality of life.

Osteoporosis is a pernicious disorder usually, but not exclusively, afflicting elderly women. The osteoporotic state can also be manifested by those who are confined to bed and even to astronauts who are subjected to prolonged weightlessness. Osteoporosis occurs through a decrease in bone mass which makes the afflicted bones more fragile and more susceptible to breaking.

The reduction in bone mass from osteoporosis results when destruction outpaces bone formation. The balance between destruction and formation is affected by hormones, calcium intake, vitamin D and its metabolites, weight, smoking, alcohol consumption, age, genetic determinants and especially exercise or other forms of dynamically loading the bone tissue as well as many other factors. Considering the vast array of factors which can compromise the healing process, any form of stimulation that can accelerate, augment and/or ensure the healing process are greatly needed.

Osteoporosis is not easily determined in its early phases as physical deformity is not yet evident. Because osteoporosis develops progressively, early diagnosis and appropriate treatment may avoid a serious condition. Appropriate diet and exercise can be used in early years to prevent the damaging effects of osteoporosis later in life. Methods for maintaining or promoting bone growth are described in numerous patents. For example, McLeod and Rubin, U.S. Pat. Nos. 5,103,806, 5,191,880, 5,273,028 and 5,376,065 collectively describe means and methods for promoting bone growth and preventing bone loss. The method described in the above referenced patents relates to a mechanical vibrational loading of bones to promote growth in a non-invasive procedure. McLeod and Rubin, U.S. Pat. Nos. 5,103,806, 5,191,880, 5,273,028 and 5,376,065 are all incorporated herein by reference. In addition, U.S. Pat. No. 5,046,484 to Basset et al. describes impact loading a patient's bones by dropping the patient from a predetermined drop excursion.

Mechanical loading on bone tissue at strains of between about 0.5 to about 500 microstrain and induced within a predetermined frequency range can prevent bone loss and enhance new bone formation. Such mechanical bone loading of tissue may be introduced by various apparatus, including vibrating floor plates and chairs, electrical stimulation of muscles, isometric exercises, modulated ultrasound or transducers attached to the skin or external fixation devices to focus energy to the fracture site.

As with osteoporosis, bone fracture may result in weakened bone structure. Improperly healed fractures are often subject to refracture. Delayed or improper union of fractures and failure of skeletal prostheses resulting from inadequate osteogenic responses lead to high morbidity and reduced quality of life. To counter these effects, many techniques have been proposed to increase bone mass and stimulate bone growth. One such technique is described in U.S. Pat. No. 4,993,413 ('413) to McLeod and Rubin which is incorporated herein by reference. The '413 patent describes a method and apparatus for inducing a current and voltage in living tissue to promote, inter alia, bone regrowth. Other techniques include the use of ultrasound waves and the application of mechanical strains directly to the fractured bone to enhance bone regrowth.

Ultrasound delivery systems use pulsed radio-frequency waves (in the MHz range) to treat bone fractures. These systems take advantage of the piezoelectric nature of bones. When ultrasound is applied to the fracture bone, the ultrasound is converted to an electric current in the bone to promote healing by small deflections within the bone. Such systems are described in U.S. Pat. Nos. 5,003,965 and 5,186,162 to Talish et al both incorporated herein by reference. The stresses induced in the bone are of the order of 100 kilopascals (kPa). The ultrasound carrier frequencies are about 1.5 MHz and higher. As the bone deflects in response to the ultrasound, bone growth is promoted. Clinical studies show that exposure of the fracture site for 20 minutes per day to such an ultrasonic stimulus will halve the time necessary to ensure a fully healed fracture.

Studies have been performed to show that cyclical mechanical stimulation has modulated the healing process. One such study is reported in Clinical Orthopedics, Clin. Ortho. & Rel. Res. (1989) 241:36–47 by J. Kenwright and A. E. Goodship (referred to hereinafter as Goodship). In the Goodship study, animals, such as sheep, were used to determine the effects of mechanical stimulation on midshaft tibial breaks of 3 mm. The regimen of treatment included a frequency loading of about 0.5 Hz, representing the walking frequency of the animal. The break or fracture was cyclically loaded for 17 minutes per day to achieve initial displacements between 0.5 mm and 2 mm. Peak stresses were permitted to reach as high as 1.8 megaPascals (MPa). It was noted that a 1 mm initial displacement yielded beneficial results. Initial displacements of greater than 1 mm resulted in an impedance to bone repair. However, Goodship used high displacements (0.5 mm to 1 mm) and stresses which may not be suitable for use in all bone repairs. Also, high displacements and stresses may increase the risk of mechanical failure of the wound healing process, as well as the failure of the fixation device itself.

Since it is desirable to enhance the rate of repair and the strength of the repair in delayed or non-union fractures, a need exists for a system and method for mechanically cycling bones at a high frequency at low levels of displacement. A need also exists for a system and method for improving bone strength in patients with osteoporosis. A further need exists for a system and method for continuing mechanical cycling treatment at different stages in the healing process.

SUMMARY

A system for therapeutic treatment of bone includes a source of energy for stimulating a bone, feedback means for receiving response information from the bone generated by the stimulation and adjustment means for adjusting the energy source according to predetermined criteria. In a biomedically based system which provides therapeutic treatment to bone disorders, a feedback means is available to modulate an output energy according to the predetermined criteria. Energy input is carefully controlled to provide proper healing to a wound site.

In alternate systems for therapeutic treatment of bone, the energy source includes a fixator coupled to the bone which may be actuated by a force. The fixator may be coupled externally to the bone or coupled to the bone interior. The energy source may also include a shaker table. The feedback means may include a data acquisition system for measuring parameters such as, force, stress and/or displacement of the bone. The adjusting means may include an actuator. The adjusting means may also include a controller for receiving feedback information and responding by proportionally adjusting a control signal to adjust the energy source according to the predetermined criteria. The predetermined criteria may include a product of displacement amplitude and force applied to the bone. The predetermined criteria may also include a ratio of stress in the bone to the frequency of stimulation. The frequency of stimulation may be between about 5 Hz to about 20 kHz.

A system for therapeutic treatment of bone fractures includes a securing apparatus for cyclically stimulating a fractured bone and properly aligning fractured portions of the bone. A feedback means for receiving response information from the fractured bone generated by the stimulation is also included. An adjustment means is used to adjust the securing apparatus according to predetermined criteria.

In alternate embodiments of the system for therapeutic treatment of bone fractures, the securing apparatus may include a fixator. The fixator may be coupled externally to the bone or coupled to the bone interior. The feedback means may include a data acquisition system for measuring parameters such as force and displacement of the bone. The adjusting means may include an actuator for actuating the securing apparatus. The adjusting means may also include a controller for receiving feedback information and responding by proportionally adjusting a control signal to adjust the securing apparatus according to the predetermined criteria. The predetermined criteria may include a product of displacement amplitude and force applied to the bone. The predetermined criteria may also include a ratio of stress in the bone to frequency of stimulation. The frequency of stimulation may be between about 5 Hz to about 20 kHz. The cyclical stimulation may include initial displacement amplitudes between fractured portions of up to 10% of the fracture gap not to exceed a ratio of stress and frequency defined in the treatment regimen.

A method of therapeutically treating bone includes the steps of providing a source of energy for stimulating a bone, feedback means for receiving response information from the bone generated by the stimulation and adjustment means for adjusting the energy source according to predetermined criteria, applying energy to cyclically stimulate the bone, collecting response information from the bone due to the stimulation, comparing the response information to the predetermined criteria and adjusting the energy source to obtain a response in accordance with the predetermined criteria.

In alternate methods of therapeutically treating bone, the step of maintaining energy in accordance with the predetermined criteria for a predetermined treatment time may be included. The predetermined treatment time may be from about 5 minutes to about 500 minutes daily. The step of applying energy to cyclically stimulate the bone may include the step of actuating the bone to create a deflection having a displacement amplitude. The loading stress may be between about 0.1 MPa to about 2 MPa. The cyclical stimulation may have a frequency between about 5 Hz to about 20 kHz. The predetermined criteria may include a value having units of stress/frequency and the step of collecting response information may further include the steps of gathering applied stress information from the bone and calculating a value of response information based on the stress information and a cyclical stimulation frequency having units of stress/frequency where the stress is an applied stress to the bone and frequency is the frequency of the cyclical stimulation. The predetermined criteria may also include a value having units of work and the step of collecting response information may further include the steps of gathering applied force and displacement information from the bone and calculating a value of response information based on the force and displacement information having units of work where work is a product of the force applied to the bone and the displacement amplitude of the cyclical stimulation. The step of adjusting may include sending an output signal from a controller which receives the response information, the output signal for adjusting the energy source to comply with the predetermined criteria. The predetermined criteria may include predetermined thresholds for stress, frequency and duration and the step of collecting response information may further include the step of adjusting one of stress, frequency and duration according the expression: $\text{Log}(\text{stress}*\text{duration}) \approx 4.5 - 0.3*\text{Log}(\text{frequency})$ where stress is a stress in the bone, frequency is a dynamic loading frequency and duration is an amount of time of treatment.

BRIEF DESCRIPTION OF DRAWINGS

The invention will be described in detail in the following description of preferred embodiments with reference to the following figures wherein.

DETAILED DESCRIPTION OF PREFERRED EMBODIMENTS

A system and method for healing bone fractures is described herein. The system is a dynamic system for applying high frequency, low displacement and low stress stimulation to a fracture site for accelerating the healing process and improving bone strength. The system includes an energy source which transfers energy to the bone. An actuator provides a force and a displacement to the bone. A feedback means collects information about predetermined parameters, for example resistance to displacement or a resistance force. The feedback means may be used to control the energy source to provide more or less energy to the bone. The actuator is thereby adjusted to provide a predetermined amount of work or energy to the broken or fractured bone joint. The actuator may be programmed to provide cyclical displacement or cyclical forces to the bone according to a formula or program. In addition, as the bone heals the actuator means is adjusted to account for smaller displacements and higher forces.

Figure 1:
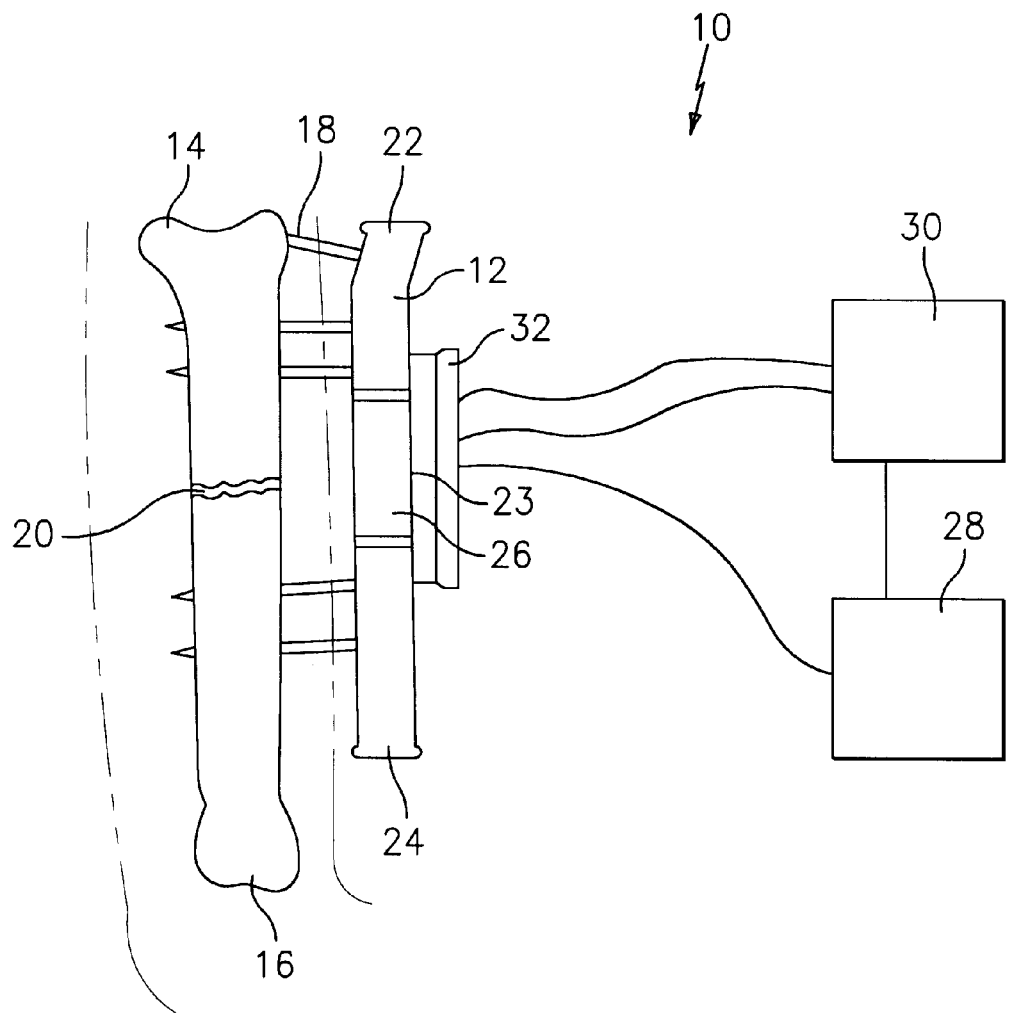
FIG. 1 is a side view of a system for therapeutic treatment of bone in accordance with the present invention.

Referring now in specific detail to the drawings in which like reference numerals identify similar or identical elements throughout the several views, and initially to FIG. 1, a system 10 is shown for therapeutically enhancing bone growth. System 10 includes an external fixator 12 which is coupled to bone portions 14 and 16 by screws or pins 18 inserted through bone portions 14 and 16. Alternately, fixator 12 may be coupled to bone portions 14 and 16 non-invasively by clamps (see FIG. 4). Fixator 12 secures bone portions 14 and 16 and acts as a strength by-pass for transferring weight across a fractured or broken portion 20. Fixator 12 has a translatable intermediate portion 23 which provides relative translation between a first end portion 22 and a second end portion 24 of fixator 12. An actuator 26 is provided to produce relative motion between first end portion 22 and second end portion 24, thereby moving bone portions 14 and 16 closer or further apart. In one embodiment, actuator 26 includes "Terfenol-D", which is a magnetostrictive material, and actuates fixator 12 proportionally to a magnetic field applied thereto. "Terfenol-D" actuators are commercially available from Etrema Products, Inc. Other actuator materials may include piezoelectric materials and the like.

Actuator 26 is controlled by a controller 28 or may be adjusted manually. Controller 28 outputs signals to control actuator 26 based on feedback information. Feedback information is based on monitored parameters which represent the present state of bone portions 14 and 16. Fixator 12 may include LVDT's for measuring dynamic displacement between bone portions 14 and 16 or actuator 26. In addition strain gauges or load cells may be used to measure displacements and forces respectively from the fixator 12, actuator 26 or bone portions 14 and 16, depending on the conditions of treatment. Data gathered for forces, strains, displacements, etc. is collected by a data acquisition system 30 and transferred to controller 28. Controller 28 processes feedback data and sends output signals to actuator 26 to modify parameters as needed.

During operation, bone portions 14 and 16 are mechanically stimulated by applying a waveform, preferably sinusoidal, at a predetermined frequency. The frequency may be selected from within a range of about 5 Hz to about 20 kHz, preferably between about 25 Hz to about 100 Hz. The power necessary to drive the actuator may be delivered by a portable power source, for example, batteries, or may be derived directly from household current.

Healing of a fracture occurs in stages, in the first stage bones are separated. Mechanical stimulation using system 10 provides displacement amplitudes preferably up to 200 microns, but never to exceed a prescribed stress, by actuating actuator 26 with a proportional control signal. As the bone portions heal, callus forms therebetween. At this point, treatment must be modified in accordance with the feedback obtained from bone portions. Displacement is decreased and force is increased by a predetermined amount. In one embodiment, the product of the force in the bone and the displacement amplitude (work) is maintained approximately constant. For example, as the bone becomes stronger more force may be applied but less deflection, thereby maintaining a relatively constant product. Other relationships between force and displacement may be derived to further improve the healing rate and bone strength as described below.

In a preferred embodiment, stress is determined within the bone by measuring the normal force directly and estimating the projected area of the bone fracture. By determining an optimal stress window, the healing rate may be further increased. An indication for the energy density imparted to the bone for a given time can be conveniently expressed as stress/frequency (Pascals/Hz) where stress is the measured or estimated stress between bone portions, and frequency is the frequency of mechanical stimulation. In this way, energy may be induced into the bone by various means to achieve a desired stress to frequency ratio.

One aspect of system 10, is a mechanical limiter 32 which prevents overloading bone portions 14 and 16 when angiogenesis and woven bone callus healing stages have begun. Initially the force applied to bone portions should be significantly less than the dynamic loads applied during normal use, for example, walking forces for a tibia. As healing ensues forces may be increased, but must remain below a threshold so as to not reverse the healing process. Mechanical limiter 32 must therefore be adjusted to account for this threshold. Mechanical limiter 32 may be a strain gauge or load cell that disables controller 28 or actuator 26 if the threshold is exceeded.

Figure 2:
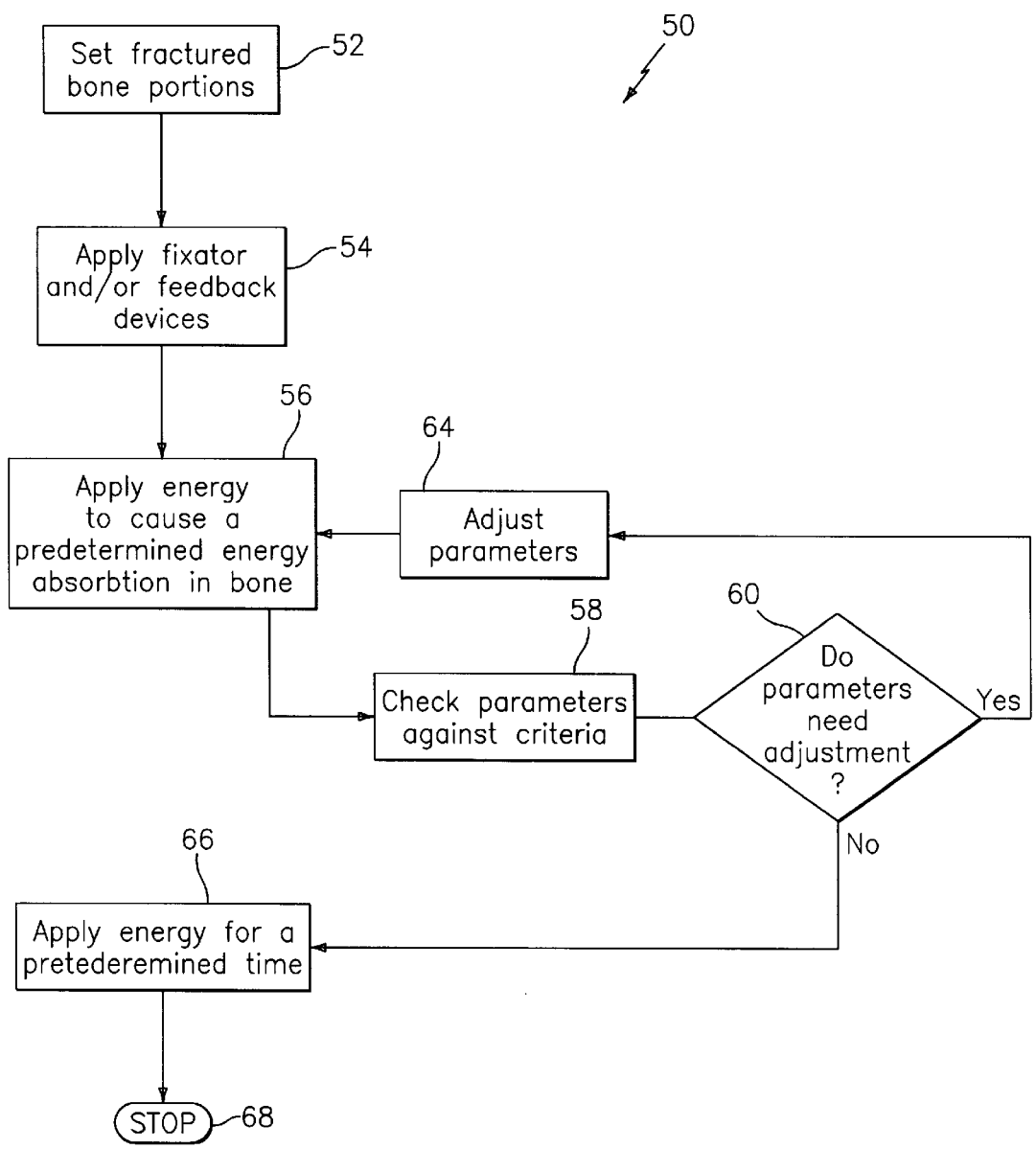
FIG. 2 is a flow chart showing a method for therapeutic treatment of bone in accordance with the present invention.

Referring to FIG. 2, a method for enhancing healing rate and increasing bone strength is shown in flow chart 50. In block 52, bone portions 14 and 16 (FIG. 1) are repositioned in proper alignment to begin the healing process. If a fixator, such as an intra-medullary nail or rod, or an external fixator, is used, it is applied in block 54. Also in block 54, any feedback equipment is setup to measure feedback parameters such as force, strain or displacement amplitude between bone portions. In block 56, initially, displacement and force are balanced to cyclically stimulate the bone fracture to provide a desired energy absorption rate. After callus begins to form, energy is applied to the bone fracture to create a stress field therein to enhance healing by absorbing energy at the fracture. Energy sources for inducing this stress field may include electrical or magnetic energy, ultrasound energy, mechanical energy, etc.

In block 58, feedback data is obtained which may include a measured force and/or displacement between bone portion during stimulation. Also calculations of formulas such as the calculation of work may be completed to determine if parameters should be adjusted. In block 60, it is decided whether the monitored parameters need to be adjusted. If adjustment is needed, criteria, such as stress/frequency, are checked to determine the amount of adjustment needed for the monitored parameters. The parameters are adjusted accordingly in block 64 and the path is returned to blocks 56, 58 and 60 until no further adjustment is necessary.

In block 66, the cyclical stimulation is applied for a predetermined amount of time. The time may range from between about 5 minutes to about 500 minutes daily, and preferably from about 10 minutes to about 30 minutes. Treatment time may be monitored by controller 28 (FIG. 1) directly and system 10 may be turned off directly when the appropriate treatment time has elapsed in block 68.

Figure 3:
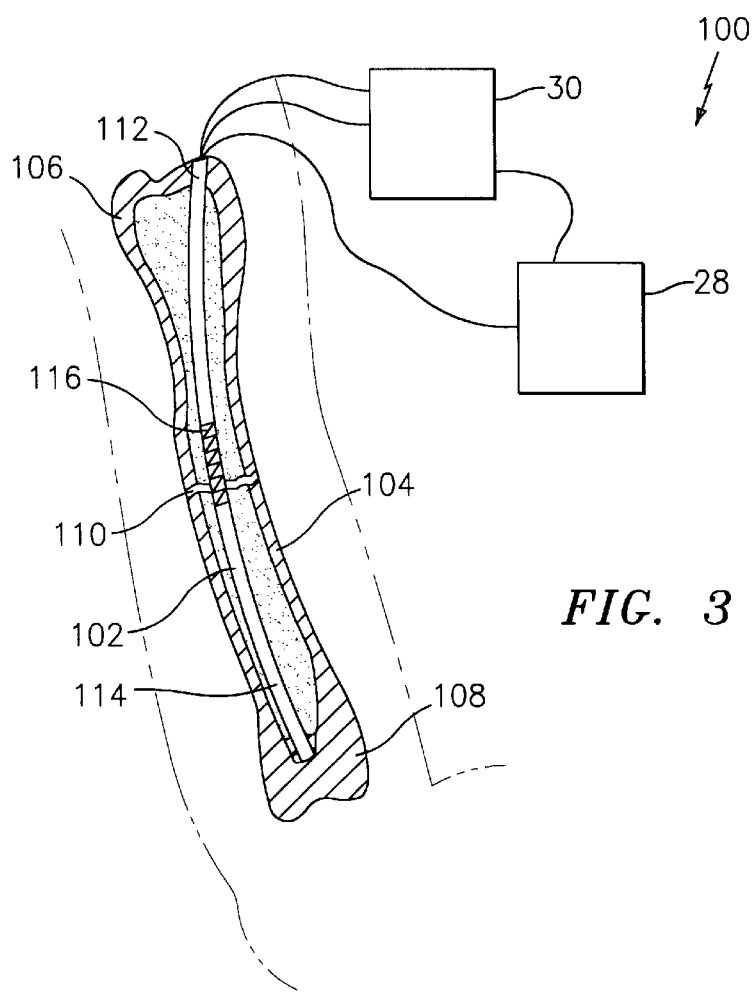
FIG. 3 is a side view in partial cross-section showing an alternate embodiment of a system for therapeutic treatment of bone.

Referring to FIG. 3, an alternate embodiment of system 10 is shown as system 100. System 100 includes an intramedullary nail or rod 102 inserted into an interior of a bone 104. Bone 104 is fractured into bone portions 106 and 108. Rod 102 provides a strength by-pass across a fracture portion 110 to transfer loads across fracture portion 110. Strain gauges and load cells may be directly mounted on rod 102 to provide feedback data to data acquisition system 30 and controller 28. Rod 102 has a first end portion 112 and a second end portion 114 which are anchored within bone 104. Rod 102 includes an actuator 116 which operates substantially as described above with reference to FIG. 1. Actuator 116 applies loads and displacements to bone 104 to enhance the healing rate in accordance with this disclosure.

Both systems 10 and 100 provide a patient with mobility. Fixator 12 and rod 102 may be disconnected from data acquisition system 30 and controller 28 to permit free movement of a recovering bone fracture patient in between treatment sessions.

Figure 4:
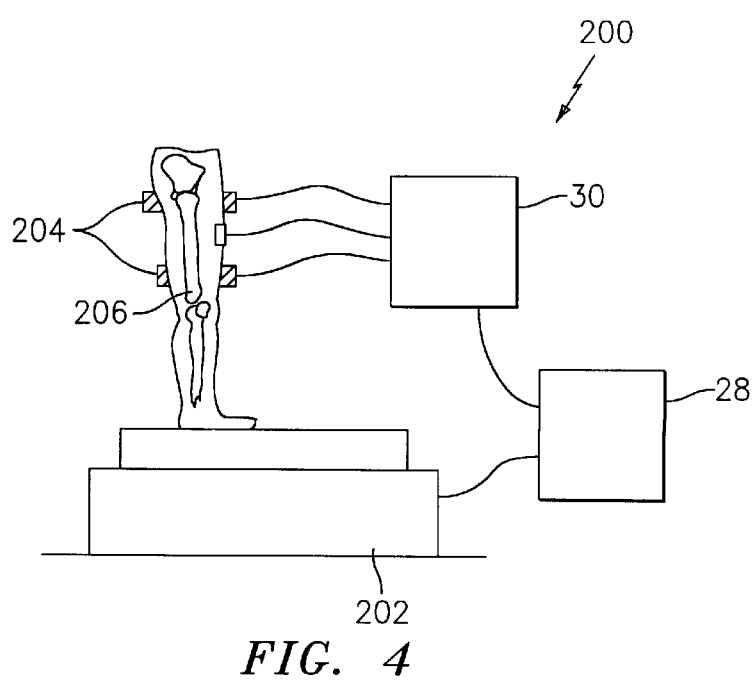
FIG. 4 is a side view showing an alternate embodiment of a system for therapeutic treatment of bone.

Referring to FIG. 4, a system 200 is shown. A patient stands on an impact or shaker table 202. Clamps 204 are externally attached to, for example a leg or legs of a patient. Clamps 204 are provided with feedback devices which monitor relative deflections between clamp positions, estimate forces applied to a bone, for example a tibia 206 and measure strain and stress within the bone being treated. Clamps 204 may include accelerometers to measure acceleration of the patient's bone to aid in estimating forces applied thereto.

Shaker table 202 functions as the actuators described above providing mechanical stimulation to the bone being treated. A cyclical excitation of shaker table 202 is used to generate a deflection within the bone being treated. Shaker table 202 parameters such as amplitude and frequency are adjusted according to feedback data collected from data acquisition system 30 by controller 28. Controller 28 supplies waveforms, preferably sinusoidal, of a given amplitude and frequency to shaker table to ensure appropriate energy absorption into the bone being treated.

Systems 10, 100 and 200 are used to treat patients according to the method described in FIG. 2. System 200 does not require block 52 and portions of block 54 which involve fixation for a bone fracture.

Figure 5:
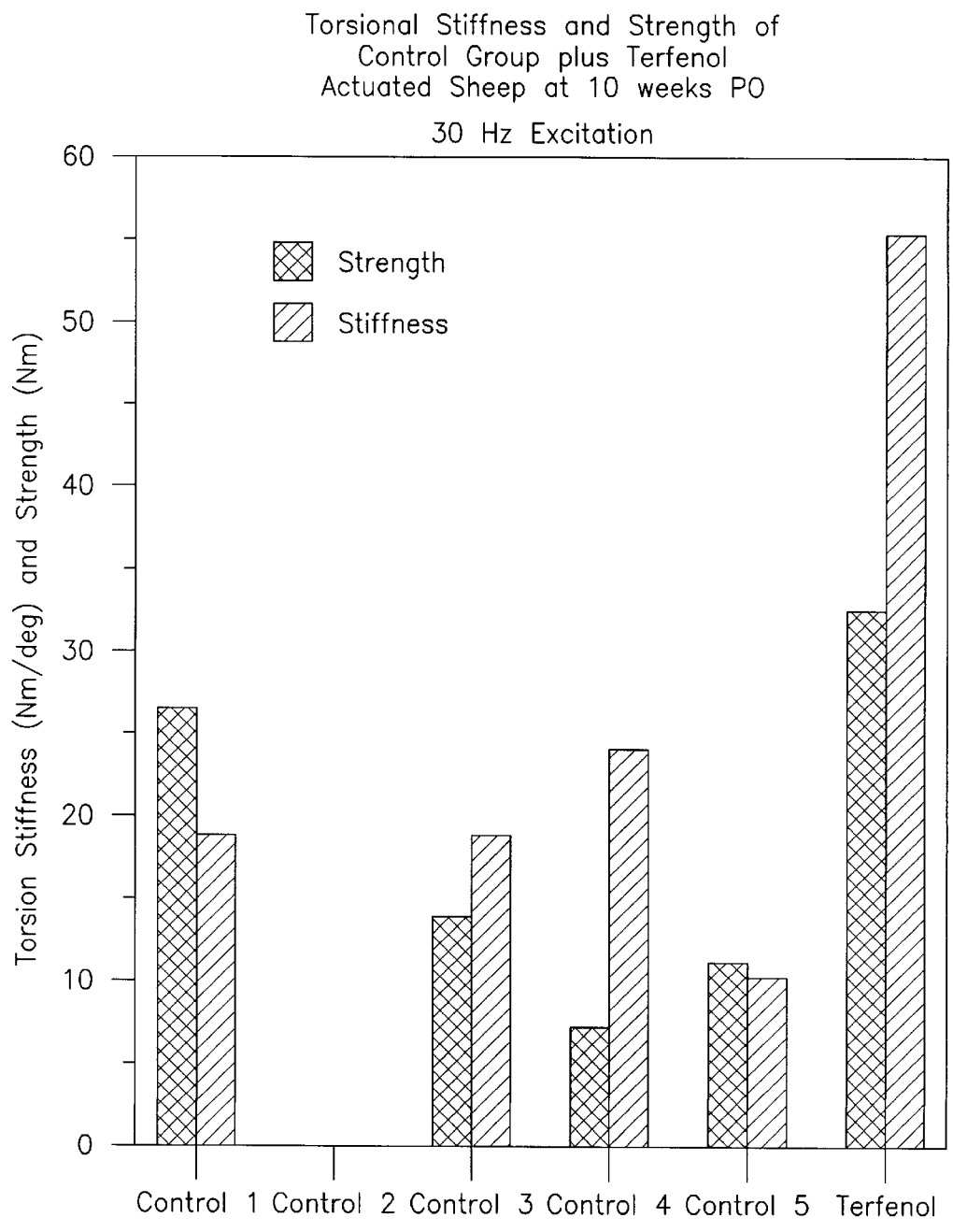
FIG. 5 is bar chart showing experimental results of torsional stiffness and strength of bones used in a study.
Figure 6:
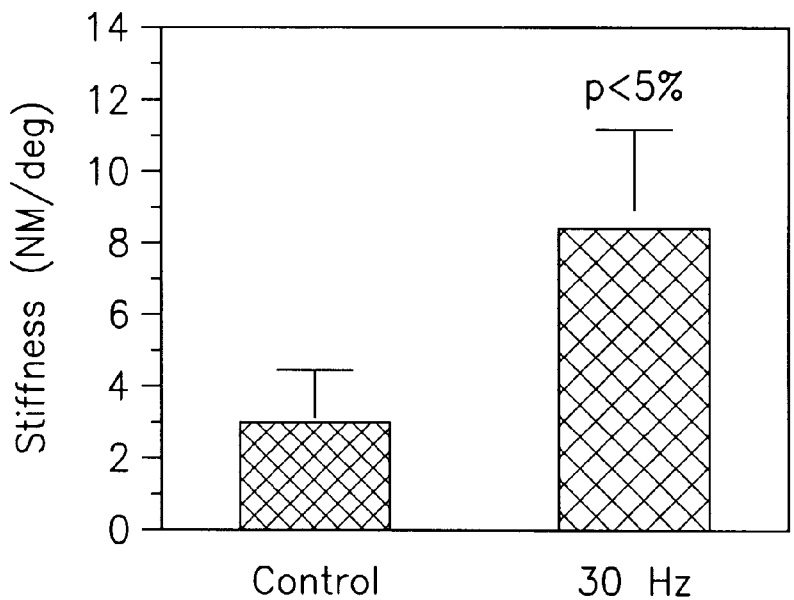
FIG. 6 is bar chart showing experimental results of torsional stiffness of bones used in a study.

Recent studies undertaken by the inventors conclusively show that smaller stresses and displacements will significantly accelerate fracture healing if the loading is undertaken at higher frequencies. In an animal study, the effect of high frequency dynamic loading on promoting healing of tibia fractures in sheep was investigated. The protocol included the utilization of an external fixator which had been modified to provide dynamic loading of the fracture site (FIG. 1). Initial displacements of about 25 micrometers were permitted across a fracture gap of approximately 3 millimeters. Peak forces were limited to about 40 Newtons, or an estimated peak stress of 350 kPa. Dynamic loading was applied at about 30 Hz for 1000 seconds per day. Fractures exposed to this treatment regimen were found to increase in torsional strength at a rate significantly faster than untreated fractures (FIG. 5). The average effect of treatment was a threefold rise in fracture callus stiffness at the end of the 10 week treatment regimen (FIG. 6). Moreover, bone mineral content was also found to be approximately threefold greater in the treatment group following 10 weeks of treatment (FIG. 7).

Referring to FIG. 5, torsional stiffness and strength of bones used in experimentation were monitored for sheep having midshaft ovine tibial 3 mm osteotomies. After 10 weeks of applying the method of FIG. 2 using system 10, strength and stiffness were measured for 5 control groups and one group using "Terfenol-D" actuators in accordance with the present invention. The control group had fractures stabilized by fixators that were locked in position. The "Terfenol-D" group experienced mechanical stimulation by actuating fixators used to stabilize the fractures. As shown in FIGS. 5 and 6, stimulated fractures had significantly more torsional stiffness ($p<5\%$) than the controls.

Figure 7:
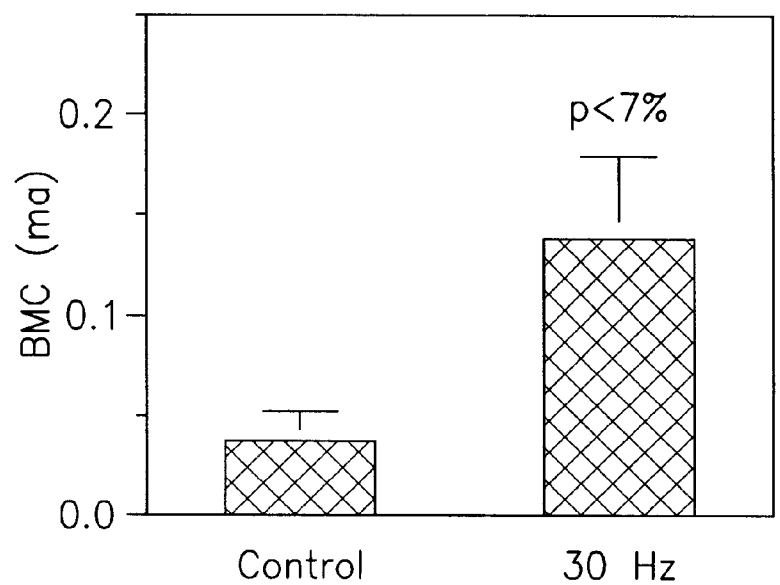
FIG. 7 is bar chart showing experimental results of bone mineral content for bones used in a study.

As shown FIG. 7, bone mineral content (BMC) data was collected. BMC in the stimulated group was significantly greater both in the fracture zone ($p<1\%$) and in four periosteal regions adjacent to the fracture gap ($p<0.1\%$).

The combined studies by the inventors on inhibition of bone loss by dynamic mechanical loading and acceleration of bone fracture healing by dynamic loading have led to the identification of an algorithm for the efficient promotion of fracture healing by dynamic loading. The algorithm relates the product of the stress applied to the fracture site and the duration of the treatment regimen to the frequency of the applied dynamic loading. These three factors can be shown to be related by the expression: $\text{Log(stress*duration)} \approx 4.5 - 0.3*\text{Log(frequency)}$ where frequency is in Hertz; stress is in kPa and duration is in minutes. This algorithm is valid through the acoustic range (from 5 kHz up to 20 kHz) and for durations extending from about 5 to about 500 minutes. During the early stages of fracture healing, stresses below this threshold level can be utilized under displacement control, until the callus is sufficiently rigid to support the above stress levels. However, displacements greater than 10% of the fracture gap are not preferred. Importantly, this algorithm demonstrates that the use of large, potentially damaging, stresses can be eliminated by either increasing the loading frequency or increasing the duration of loading or both. Stresses more than twice the above prescribed levels should be avoided, as they may contribute to the incidence of delayed or non-union. Because for a given modulus of the bone tissue, a stress can be converted to a strain within the tissue, the above formulation may alternatively be viewed as energy transfer needed to the fracture site. As the modulus of the fracture site changes dramatically as a function of time and healing (e.g. phases of inflammation, repair and remodeling), conversion to strain requires that the displacements output by the device will change as a complex interdependent function of time and stage of healing.

Having described preferred embodiments of a method and system for healing bone fractures and treating osteoporosis (which are intended to be illustrative and not limiting), it is noted that the modifications and variations could be made by those skilled in the art in light of the above teachings. It is therefore to be understood that changes may be made in the particular embodiments of the invention disclosed which are within the scope and spirit of the invention defined by the appended claims.

What is claimed is:

1. A system for therapeutic treatment of bone fractures comprising:
   a securing apparatus for cyclically stimulating a fractured bone and properly aligning fractured portions of the bone;
   feedback means for receiving response information from the fractured bone generated by the stimulation; and
   adjustment means for adjusting the securing apparatus according to predetermined criteria.

2. The system for therapeutic treatment of bone fractures as recited in claim 1, wherein the securing apparatus includes a fixator.

3. The system for therapeutic treatment of bone fractures as recited in claim 2, wherein the fixator is coupled externally to the bone.

4. The system for therapeutic treatment of bone fractures as recited in claim 2, wherein the fixator is coupled to the bone interior.

5. The system for therapeutic treatment of bone fractures as recited in claim 1, wherein the feedback means includes a data acquisition system and the response information includes stress and displacement information from the bone.

6. The system for therapeutic treatment of bone fractures as recited in claim 1, wherein the adjusting means includes an actuator for actuating the securing apparatus.

7. The system for therapeutic treatment of bone fractures as recited in claim 1, wherein the adjusting means includes a controller for receiving feedback information and responding by proportionally adjusting a control signal to adjust the securing apparatus according to the predetermined criteria.

8. The system for therapeutic treatment of bone fractures as recited in claim 1, wherein the predetermined criteria includes a product of displacement amplitude and force applied to the bone.

9. The system for therapeutic treatment of bone fractures as recited in claim 1, wherein the predetermined criteria includes a ratio of stress in the bone to frequency of stimulation.

10. The system for therapeutic treatment of bone fractures as recited in claim 9, wherein the frequency of stimulation is between about 5 Hz to about 20 kHz.

11. The system for therapeutic treatment of bone fractures as recited in claim 1, wherein the predetermined criteria includes maintaining parameters according the expression: $Log(stress*duration) \approx 4.5 - 0.3*Log(frequency)$ where stress is a stress in the bone, frequency is a dynamic loading frequency and duration is an amount of time of treatment.

12. The system for therapeutic treatment of bone fractures as recited in claim 1, wherein the cyclical stimulation includes displacement amplitudes of fractured portions of up to about 200 microns and less than a threshold stress level.

* * * * *